United States Patent
Quintaine et al.

(10) Patent No.: US 11,319,272 B2
(45) Date of Patent: May 3, 2022

(54) ALPHA ALKYLATION OF ALDEHYDE WITH A POLYCYCLIC OLEFIN

(71) Applicant: FIRMENICH SA, Geneva (CH)

(72) Inventors: Julie Quintaine, Geneva (CH); David W. C. MacMillan, Princeton, NJ (US)

(73) Assignee: FIRMENICH SA, Geneva (CH)

( * ) Notice: Subject to any disclaimer, the term of this patent is extended or adjusted under 35 U.S.C. 154(b) by 256 days.

(21) Appl. No.: 16/605,309

(22) PCT Filed: Apr. 17, 2018

(86) PCT No.: PCT/EP2018/059780
§ 371 (c)(1),
(2) Date: Oct. 15, 2019

(87) PCT Pub. No.: WO2018/192923
PCT Pub. Date: Oct. 25, 2018

(65) Prior Publication Data
US 2021/0147328 A1    May 20, 2021

Related U.S. Application Data

(60) Provisional application No. 62/486,695, filed on Apr. 18, 2017.

(30) Foreign Application Priority Data

May 4, 2017 (EP) .................................... 17169442

(51) Int. Cl.
| C07C 45/68 | (2006.01) |
| C11B 9/00 | (2006.01) |
| C07C 47/225 | (2006.01) |
| A61K 8/33 | (2006.01) |
| A61Q 5/02 | (2006.01) |
| A61Q 13/00 | (2006.01) |
| A61Q 19/10 | (2006.01) |
| B01J 31/22 | (2006.01) |
| C07C 45/69 | (2006.01) |
| C07C 47/115 | (2006.01) |
| C11D 3/00 | (2006.01) |
| C11D 3/50 | (2006.01) |

(52) U.S. Cl.
CPC .............. *C07C 47/225* (2013.01); *A61K 8/33* (2013.01); *A61Q 5/02* (2013.01); *A61Q 13/00* (2013.01); *A61Q 19/10* (2013.01); *B01J 31/22* (2013.01); *C07C 45/69* (2013.01); *C07C 47/115* (2013.01); *C11B 9/0034* (2013.01); *C11B 9/0046* (2013.01); *C11D 3/001* (2013.01); *C11D 3/50* (2013.01); *B01J 2231/005* (2013.01); *B01J 2531/827* (2013.01); *C07C 2601/16* (2017.05); *C07C 2602/42* (2017.05)

(58) Field of Classification Search
CPC ........ C07C 45/68; C07C 45/69; C11B 9/0034; C11B 9/0038
See application file for complete search history.

(56) References Cited

U.S. PATENT DOCUMENTS

| 3,780,109 A | 12/1973 | Schleppnik |
| 4,396,670 A | 8/1983 | Sinclair |
| 6,376,458 B1 | 4/2002 | Winter |
| 2013/0090390 A1 | 11/2013 | Singer et al. |

FOREIGN PATENT DOCUMENTS

| EP | 2578671 A1 | 4/2013 |
| WO | 01/41915 A1 | 6/2001 |
| WO | 2005079573 A1 | 9/2005 |

OTHER PUBLICATIONS

International Search Report and Written Opinion for International Application No. PCT/EP2018/059780, dated Jun. 20, 2018. 15 pages.
Bone et al., "Microencapsulated Fragrances in Melamine Formaldehyde Resins", Chimia, 2011, pp. 177-181, vol. 65-3.
Lee et al., "Microencapsulation of fragrant oil via in situ polymerization: effects of pH and melamine-fomaldehyde molar ratio", Journal of Microencapsulation, 2002, pp. 559-569, vol. 19-5.
Nicewicz et al., "Merging Photoredox Catalysis with Organocatalysis: The Direct Asymmetric Alkylation of Aldehydes", Science, 2008, pp. 77-80, vol. 322.
Dietrich et al., "Amino resin microcapsules", Acta Polymerica, 1989, pp. 243-251, vol. 40-4.
Dietrich et al., "Amino resin microcapsules", Acta Polymerica, 1989, pp. 683-690, vol. 40-11.

(Continued)

*Primary Examiner* — Sikarl A Witherspoon
(74) *Attorney, Agent, or Firm* — Armstrong Teasdale LLP

(57) ABSTRACT

The alpha alkylation of an aldehyde with a polycyclic olefin followed by a ring opening step is presented in order to provide a compound of formula (I) in the form of any one of its stereoisomers or a mixture thereof and where in R represents a hydrogen atom or $C_{1-8}$ linear alkyl group; $R^1$, $R^2$, $R^3$, and $R^4$ represent, when taken separately, independently of each other, a hydrogen atom or a $C_{1-2}$ linear alkyl group or a $C_{3-4}$ linear or branched alkyl group; or $R^2$ and $R^3$, when taken together, represent a $C_{4-10}$ linear, branched or cyclic alkanediyl group and n is 1 or 2 is presented.

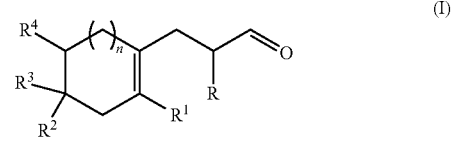

(I)

16 Claims, No Drawings

(56) References Cited

OTHER PUBLICATIONS

Dietrich et al., "Amino resin microcapsules", Acta Polymerica, 1990, pp. 91-95, vol. 41-2.
Terrett et al., "Direct B-Alkylation of Aldehydes via Photoredox Organocatalysis", Journal of the American Chemical Society, 2014, pp. 6858-6861, vol. 136.

ized alkyl group; or $R^2$ and $R^3$, when taken together, represent a $C_{4-10}$

ALPHA ALKYLATION OF ALDEHYDE WITH A POLYCYCLIC OLEFIN

CROSS-REFERENCE TO RELATED APPLICATIONS

This application is a U.S. National Phase Application of PCT/EP2018/059780, filed on Apr. 17, 2018, which claims the benefit of priority to European Patent Application Number 17169442.5, filed May 4, 2017, and to U.S. Provisional Application No. 62/486,695, filed on Apr. 18, 2017, the entire contents of which are hereby incorporated by reference herein.

TECHNICAL FIELD

The present invention relates to the field of organic synthesis and more specifically to the alpha alkylation of an aldehyde with a strained polycyclic olefin followed by a ring opening step in order to provide a compound of formula (I). The composition of matter obtainable by such a process, the use of said composition of matter and a perfuming composition or a perfuming consumer product comprising said composition of matter are also part of the present invention.

PRIOR ART

One pot processes comprising several steps are much appreciated in organic synthesis as they lead to the formation of complex chemical structures starting from simple starting materials. For example, the one pot alpha alkylation of an aldehyde with a polycyclic olefin followed by a ring opening step provides a compound of formula (I). Said process allows avoiding a multi-step process toward compound of formula (I).

To the best of our knowledge, said addition/ring opening process has been reported in *Comptes Rendus Hebdomadaires des Séances de l'Académie des Sciences* 1967, 525 and in *Comptes Rendus Hebdomadaires des Séances de l'Académie des Sciences* 1970, 63. However, the radical addition of a linear aldehyde on β-pinene provides a mixture of a ketone and 3-(4-isopropylcyclohex-1-en-1-yl)-2-alkyl-propanal. When propanal is used as an aldehyde, only 14.38% of 3-(4-isopropylcyclohex-1-en-1-yl)-2-methylpropanal have been isolated.

So, there is a need to improve reaction conditions of the alpha alkylation of an aldehyde with a strained polycyclic olefin followed by a ring opening step in order to favor the formation of compound of formula (I).

The present invention provides a solution to the above problem by performing said alpha alkylation of a linear aldehyde with a polycyclic olefin in the presence of a photoredox catalyst, a hydrogen atom transfer donor, a secondary amine and light. The alkylation of an aldehyde using a secondary amine and a photoredox catalyst has been reported in Journal of American Chemical Society 2014, 136, 6859. However under described conditions the beta alkylation is observed. To the best of our knowledge, this process has never been reported.

SUMMARY OF THE INVENTION

The invention relates to a novel process providing a compound of formula (I) through the alpha alkylation of an aldehyde with a polycyclic olefin followed by a ring opening step which allows avoiding a multistep process while favoring the formation of compound of formula (I).

So, a first object of the present invention is a process for the preparation of a compound of formula

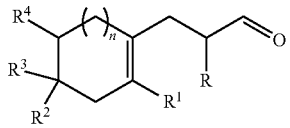

in the form of any one of its stereoisomers or a mixture thereof and wherein R represents a hydrogen atom or $C_{1-8}$ linear alkyl group; $R^1$, $R^2$, $R^3$ and $R^4$ represent, when taken separately, independently of each other, a hydrogen atom or a $C_{1-2}$ linear alkyl group or a $C_{3-4}$ linear or branched alkyl group; or $R^2$ and $R^3$, when taken together, represent a $C_{4-10}$ linear, branched or cyclic alkanediyl group and n is 1 or 2; comprising the step of an alpha alkylation of an aldehyde of formula R—$CH_2$—CHO wherein R has the same meaning than above with an olefin compound being a fused or bridged bicyclic or tricyclic compound with a methylene group in alpha of a ring junction;

said step being performed in the presence of a photoredox catalyst, a hydrogen atom transfer donor, a secondary amine and light.

A second object of the present invention is a composition of matter comprising a) a compound of formula

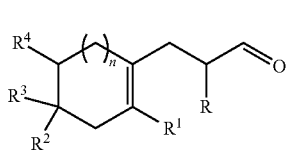

in the form of any one of its stereoisomers or a mixture thereof and wherein R represents a hydrogen atom or $C_{1-8}$ linear alkyl group; $R^1$, $R^2$, $R^3$ and $R^4$ represent, when taken separately, independently of each other, a hydrogen atom or a $C_{1-2}$ linear alkyl group or a $C_{3-4}$ linear or branched alkyl group or $R^2$ and $R^3$, when taken together, represent a $C_{4-10}$ linear, branched or cyclic alkanediyl group and n is 1 or 2; and b) a compound of formula

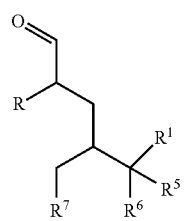

in the form of any one of its stereoisomers or a mixture thereof; and wherein R represents a hydrogen atom or a $C_{1-8}$ linear alkyl group; $R^1$ represents a hydrogen atom or a $C_{1-2}$ linear alkyl group or a $C_{3-4}$ linear or branched alkyl group; and $R^5$, $R^6$ and $R^7$ are taken together and represent a $C_{4-12}$ linear, branched or alicyclic alkanetryil.

A third object of the invention is a method to confer, enhance, improve or modify the odor properties of a perfuming composition or of a perfumed article, which method comprises adding to said composition or article an effective amount of the composition of matter as defined above.

Another object of the invention is the use as a perfuming ingredient of a composition of matter as defined above.

Another object of the invention is a perfuming composition comprising
i) at least a composition of matter as defined above;
ii) at least one ingredient selected from the group consisting of a perfumery carrier and a perfumery base; and
iii) optionally at least one perfumery adjuvant.

A last object of the invention is a perfumed consumer product comprising at least one composition of matter as defined above or a perfuming composition as defined above.

DESCRIPTION OF THE INVENTION

It has now been discovered that the compound of formula (I) can be produced in an advantageous manner by means of alpha alkylation of an aldehyde with a strained polycyclic olefin followed by a ring opening step. Said process allows avoiding the formation of ketone side product.

A first object of the present invention is a process for the preparation of a compound of formula

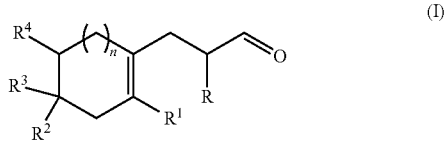

in the form of any one of its stereoisomers or a mixture thereof and wherein R represents a hydrogen atom or $C_{1-8}$ linear alkyl group; $R^1$, $R^2$, $R^3$ and $R^4$ represent, when taken separately, independently from each other, a hydrogen atom or a $C_{1-2}$ linear alkyl group or a $C_{3-4}$ linear or branched alkyl group; or $R^2$ and $R^3$, when taken together, represent a $C_{4-10}$ linear, branched or cyclic alkanediyl group and n is 1 or 2; comprising the step of an alpha alkylation of an aldehyde of formula R—CH$_2$—CHO wherein R has the same meaning than above with an olefin compound being a fused or bridged bicyclic or tricyclic compound with a methylene group in alpha of a ring junction;
said step being performed in the presence of a photoredox catalyst, a hydrogen atom transfer donor, a secondary amine and light.

Said alkylation is followed by a ring opening.

For the sake of clarity, by the expression "any one of its stereoisomers or a mixture thereof", or the similar, it is meant the normal meaning understood by a person skilled in the art, i.e. that the compound of formula (I) can be a pure enantiomer or diastereomer. In other words, the compound of formula (I) may possess several stereocenters and each of said stereocenter can have two different stereochemistries (e.g. R or S). The compound of formula (I) may even be in the form of a pure enantiomer or in the form of a mixture of enantiomers or diastereoisomers. The compound of formula (I) can be in a racemic form or scalemic form. Therefore the compound of formula (I) can be one stereoisomers or in the form of a composition of matter comprising, or consisting of, various stereoisomers.

By the expression "$R^2$ and $R^3$, when taken together, represent a $C_{4-10}$ linear, branched or cyclic alkanediyl group", or similar, it is meant the normal meaning in the art; i.e. compound of formula (I) is a bicyclic compound. In other word, $R^2$ and $R^3$ when taken together, represent a divalent alkyl group.

By the term "fused or bridged bicyclic or tryclic compound" or similar, it is meant the normal meaning in the art, i.e. for fused bicyclic compound, the compound comprises two ring sharing two adjacent atoms; e.g. decaline and for bridged bicyclic compound, the compound comprise two ring sharing at least three atoms, e.g. norbornane provided that fused or bridged bicyclic or tryclic compound does not comprise a fused cyclopropyl ring.

By the term "methylene" or similar, it is meant the normal meaning in the art, i.e. a CH$_2$ group linked to one carbon of the cycle by a double bond. In other word, olefin compound has a terminal exo double bond.

By the term "secondary amine", it is meant the normal meaning in the art, i.e. the nitrogen atom is substituted by one hydrogen atoms and two groups different than hydrogen atom.

For the sake of clarity, by the term "photoredox catalyst", it is meant the normal meaning in the art, i.e. a catalyst absorbing light to accelerate a chemical reaction by activating of organic substrates via a single electron transfer process.

For the sake of clarity, by the expression "hydrogen atom transfer donor", it is meant the normal meaning in the art, i.e. a compound able to provide a hydrogen free radical. Hydrogen atom transfer is also called HAT.

According to any one of the above embodiments, R may be a hydrogen atom or a $C_{1-8}$ linear alkyl group. Preferably, R may be a $C_{1-3}$ linear alkyl group; i.e. the aldehyde may be selected from the group consisting of propanal, butanal and pentanal. Preferably, R may be a methyl or an ethyl group; i.e. the aldehyde may be selected from the group consisting of propanal and butanal. Even more preferably, R may be a methyl group; i.e. the aldehyde may be propanal.

According to any one of the above embodiments, $R^1$ represents a hydrogen atom or a $C_{1-2}$ linear alkyl group or a $C_{3-4}$ linear or branched alkyl group. Preferably, $R^1$ may be a hydrogen atom, a methyl group or an ethyl group. Even more preferably, $R^1$ may be a hydrogen atom or a methyl group.

According to any one of the above embodiments, $R^2$ represents a hydrogen atom or a $C_{1-2}$ linear alkyl group or a $C_{3-4}$ linear or branched alkyl group. Preferably, $R^2$ may be a hydrogen atom or a $C_{1-2}$ linear alkyl group or a $C_3$ linear or branched alkyl group. Even more preferably, $R^2$ may be a hydrogen atom or an isopropyl group.

According to any one of the above embodiments, $R^3$ represents a hydrogen atom or a $C_{1-2}$ linear alkyl group or a $C_{3-4}$ linear or branched alkyl group. Preferably, $R^3$ may be a hydrogen atom or a $C_{1-2}$ linear alkyl group or a $C_3$ linear or branched alkyl group. Preferably, $R^3$ may be a hydrogen atom or a $C_{1-2}$ linear alkyl group. Even more preferably, $R^3$ may be a hydrogen atom.

According to any one of the above embodiments, $R^4$ represents a hydrogen atom or a $C_{1-2}$ linear alkyl group or a $C_{3-4}$ linear or branched alkyl group. Preferably, $R^4$ may be a hydrogen atom or a $C_{1-2}$ linear alkyl group or a $C_3$ linear or branched alkyl group. Even more preferably, $R^4$ may be a hydrogen atom.

According to any one of the above embodiments, $R^2$ and $R^3$, when taken together, represent a $C_{4-10}$ linear, branched or cyclic alkanediyl group. Preferably, $R^2$ and $R^3$, when taken together, may represent a $C_{6-9}$ linear, branched or cyclic alkanediyl group. Even more preferably, $R^2$ and $R^3$, when taken together, may represent a $C_{6-9}$ branched alkanediyl group. Even more preferably, $R^2$ and $R^3$, when taken together, may represent 2-methylhept-3,6-diyl.

According to any one of the above embodiments, n is 1 or 2. Preferably, n may be 1.

According to any one of the above embodiments, the compound of formula (I) is selected from the group consisting of 3-(4-isopropylcyclohex-1-en-1-yl)-2-methylpropanal and 3-((S)-4-isopropylcyclohex-1-en-1-yl)-2-methylpropanal.

According to any one of the above embodiments, the olefin may be a compound of formula (II)

in the form of any one of its stereoisomers or a mixture thereof; and wherein $R^1$ represents a hydrogen atom or a $C_{1-2}$ linear alkyl group or a $C_{3-4}$ linear or branched alkyl group and $R^5$, $R^6$ and $R^7$ are taken together and represent a $C_{4-12}$ linear, branched or alicyclic alkanetryil.

By the expression "$R^5$, $R^6$ and $R^7$ when taken together, represent a $C_{4-12}$ linear, branched or alicyclic alkanetryil", or similar, it is meant the normal meaning in the art; i.e. compound of formula (II) is a bicyclic or tricyclic compound. In other word, $R^5$, $R^6$ and $R^7$ when taken together, represent a trivalent alkyl group.

According to any one of the above embodiments, compound of formula (II) does not comprise a fused cyclopropyl ring.

According to any one of the above embodiments, $R^5$, $R^6$ and $R^7$ are taken together and represent a $C_{4-12}$ linear, branched or alicyclic alkanetryil. Preferably, $R^5$, $R^6$ and $R^7$ are taken together and represent a $C_{4-12}$ linear, branched or alicyclic alkanetryil provided that compound of formula (II) does not comprise a fused cyclopropyl ring. Preferably, $R^5$, $R^6$ and $R^7$ are taken together and represent a $C_{4-11}$ branched or alicyclic alkanetryil group. Even more preferably, $R^5$, $R^6$ and $R^7$ are taken together and represent a $C_{4-6}$ branched alkanetryil group. Even more preferably, $R^5$, $R^6$ and $R^7$ are taken together and represent a $C_{4-6}$ branched alkanetryil group provided that compound of formula (II) does not comprise a fused cyclopropyl ring.

According to any embodiments of the invention, and independently of the specific aspects, the compound (I), as well as the compound (II), can be in the form of a racemate or in a form of any one of its stereo isomers or mixture thereof. For the sake of clarity by the term stereoisomer it is intended any diastereomer or enantiomer.

Indeed, the compound (I) or (II) may have several stereogenic centers which can have different stereochemistry (i.e. when two stereogenic centers are present, compound (I) or (II) can have (R,R) or (R,S) configuration). Each of said stereogenic centers can be in a relative or absolute configuration R or S or a mixture thereof or in other words said compound of formula (I) or (II) can be in a form of pure enantiomer or diastereoisomer, or in a form of a mixture of stereoisomers.

According to a particular embodiment, the olefin may be a compound of formula (III)

in the form of any one of its stereoisomers or a mixture thereof; and wherein p is 0 or 1; $R^1$, $R^9$, $R^{10}$, $R^{11}$ $R^{12}$ and $R^{13}$ represent, when taken separately, independently from each other, a hydrogen atom or a $C_{1-2}$ linear alkyl group or a $C_{3-5}$ linear or branched alkyl group; or $R^8$ and $R^9$ represent, when taken together, a $C_2$ linear alkanediyl group or a $C_{3-4}$ linear or branched alkanediyl group; or $R^8$ and $R^{11}$ represent, when taken together, a $C_{1-2}$ linear alkanediyl group or a $C_{3-4}$ linear or branched alkanediyl group; or $R^8$ and $R^{13}$ represent, when taken together, a $C_{1-2}$ linear alkanediyl group or a $C_{3-4}$ linear or branched alkanediyl group; or $R^8$, $R^{11}$ and $R^{12}$ represent, when taken together, a $C_{3-10}$ linear or branched alkanetriyl group; provided that $R^8$ and $R^9$ or $R^8$ and $R^{11}$ or $R^8$ and $R^{13}$ or $R^8$, $R^{11}$ and $R^{12}$ are taken together.

By the expression "$R^8$ and $R^9$ represent, when taken together, a $C_2$ linear alkanediyl group or a $C_{3-4}$ linear or branched alkanediyl group" it is meant that $R^8$ and $R^9$ do not represent, when taken together, a 1,1-methanediyl or a substituted 1,1-methanediyl.

By the expression "provided that $R^8$ and $R^9$ or $R^8$ and $R^{11}$ or $R^8$ and $R^{13}$ or $R^8$, $R^{11}$ and $R^{12}$ are taken together" or similar, it is meant the normal meaning in the art; i.e. that the compound of formula (III) is a bicyclic or a tricyclic compound wherein the methylene group is in alpha position of a ring junction providing that compound of formula (III) does not comprise a fused cyclopropyl ring.

According to a particular embodiment, the olefin may be a compound of formula (III)

in the form of any one of its stereoisomers or a mixture thereof; and wherein p is 0 or 1; $R^1$, $R^9$, $R^{10}$, $R^{11}$ $R^{12}$ and $R^{13}$ represent, when taken separately, independently from each other, a hydrogen atom or a $C_{1-2}$ linear alkyl group or a $C_{3-5}$ linear or branched alkyl group; or $R^8$ and $R^{11}$ represent, when taken together, a $C_{1-2}$ linear alkanediyl group or a $C_{3-4}$ linear or branched alkanediyl group; or $R^8$ and $R^{13}$ represent, when taken together, a $C_{1-2}$ linear alkanediyl group or a $C_{3-4}$ linear or branched alkanediyl group; or $R^8$, $R^{11}$ and $R^{12}$ represent, when taken together, a $C_{3-10}$ linear or branched alkanetriyl group; provided that $R^8$ and $R^{11}$ or $R^8$ and $R^{13}$ or $R^8$, $R^{11}$ and $R^{12}$ are taken together.

According to a particular embodiment, the olefin may be a compound of formula

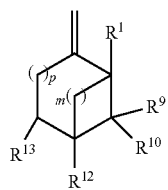

(IV)

in the form of any one of its stereoisomers or a mixture thereof; and wherein p is an integer between 0 and 1; m is 1 or 2; and $R^1$, $R^9$, $R^{10}$, $R^{12}$ and $R^{13}$ represent, when taken separately, independently from each other, a hydrogen atom or a $C_{1-2}$ linear alkyl group or a $C_{3-5}$ linear or branched alkyl.

According to any one of the above embodiments, $R^9$ represents a hydrogen atom, a $C_{1-2}$ linear alkyl group or a $C_{3-5}$ linear or branched alkyl group. Preferably, $R^9$ may represent a hydrogen atom, a $C_{1-2}$ linear alkyl group or a $C_{3-4}$ linear or branched alkyl group. Even more preferably, $R^9$ may represent a hydrogen atom or a methyl group.

According to any one of the above embodiments, $R^{10}$ represents a hydrogen atom, a $C_{1-2}$ linear alkyl group or a $C_{3-5}$ linear or branched alkyl group. Preferably, $R^{10}$ may represent a hydrogen atom, a $C_{1-2}$ linear alkyl group or a $C_{3-4}$ linear or branched alkyl group. Preferably, $R^{10}$ may represent a hydrogen atom, a methyl group or an isopropyl group. Even more preferably, $R^{10}$ may represent a hydrogen atom or a methyl group.

According to any one of the above embodiments, $R^{11}$ represents a hydrogen atom, a $C_{1-2}$ linear alkyl group or a $C_{3-5}$ linear or branched alkyl group. Preferably, $R^{11}$ may represent a hydrogen atom, a $C_{1-2}$ linear alkyl group or a $C_{3-4}$ linear or branched alkyl group. Preferably, $R^{11}$ may represent a hydrogen atom or a methyl group. Even more preferably, $R^{11}$ may represent a hydrogen atom.

According to any one of the above embodiments, $R^{12}$ represents a hydrogen atom, a $C_{1-2}$ linear alkyl group or a $C_{3-5}$ linear or branched alkyl group. Preferably, $R^{12}$ may represent a hydrogen atom, a $C_{1-2}$ linear alkyl group or a $C_{3-4}$ linear or branched alkyl group. Preferably, $R^{12}$ may represent a hydrogen atom or a methyl group. Even more preferably, $R^{12}$ may represent a hydrogen atom.

According to any one of the above embodiments, $R^{13}$ represents a hydrogen atom, a $C_{1-2}$ linear alkyl group or a $C_{3-5}$ linear or branched alkyl group. Preferably, $R^{13}$ may represent a hydrogen atom, a $C_{1-2}$ linear alkyl group or a $C_{3-4}$ linear or branched alkyl group. Even more preferably, $R^{13}$ may represent a hydrogen atom.

According to any one of the above embodiments, $R^8$ and $R^9$ represent, when taken together, a $C_2$ linear alkanediyl group or a $C_{3-4}$ linear or branched alkanediyl group. R and $R^9$ do not represent, when taken together, a 1,1-methanediyl or a substituted 1,1-methanediyl.

According to any one of the above embodiments, $R^8$ and $R^{11}$ represent, when taken together, a $C_{1-2}$ linear alkanediyl group or a $C_{3-4}$ linear or branched alkanediyl group. Preferably, $R^8$ and $R^{11}$ may represent, when taken together, a methanediyl group or a propane-2,2-diyl.

According to any one of the above embodiments, $R^8$ and $R^{13}$ represent, when taken together, a $C_{1-2}$ linear alkanediyl group or a $C_{3-4}$ linear or branched alkanediyl group. Preferably, $R^8$ and $R^{13}$ may represent, when taken together, a methanediyl group or a propane-2,2-diyl.

According to any one of the above embodiments, $R^8$, $R^{11}$ and $R^{12}$ represent, when taken together, a $C_{3-10}$ linear or branched alkanetriyl group. Preferably, $R^8$, $R^{11}$ and $R^{12}$ may represent, when taken together, a $C_{7-9}$ branched alkanetriyl group.

According to any one of the above embodiments, p is an integer between 0 and 1. Preferably p is 1.

According to any one of the above embodiments m is 1 or 2. Preferably, m is 1.

Non-limiting examples of olefin may include β-pinene and β-cedrene. Said olefin may be in a racemic form or in an enantiomerically enriched form or in an enantiomerically pure form. Preferably, the olefin may be (−)-β-pinene According to any one of the above embodiments, the olefin can be added into the reaction medium of the invention's process in a large range of concentrations. As non-limiting examples, one can cite as olefin concentration values those ranging from about 1 mole equivalent to about 8 mole equivalents, relative to the amount of the aldehyde, preferably from about 1.2 mole equivalents to about 6 mole equivalents, relative to the amount of the aldehyde, 1.8 mole equivalents to about 3.5 mole equivalents, relative to the amount of the aldehyde. The optimum concentration of the olefin will depend, as the person skilled in the art knows, on the nature of the latter, on the nature of the aldehyde, the hydrogen atom transfer donor, the photoredox catalyst and/or the secondary amine, on the reaction temperature as well as on the desired time of reaction.

According to any one of the above embodiments, the photoredox catalyst may be an organic photocatalyst, or an iridium or a ruthenium complex, preferably, an iridium complex.

According to any one of the above embodiments, the photoredox catalyst may have a redox potential of at least 0.8V vs. SCE.

According to a particular embodiment, non-limiting examples of suitable photoredox catalyst may include [4,4'-Bis(1,1-dimethylethyl)-2,2'-bipyridine-N1,N1']bis[3,5-difluoro-2-[5-(trifluoromethyl)-2-pyridinyl-N]phenyl-C]Iridium$^{(III)}$ hexafluorophosphate (corresponding to Ir(dF(CF3)ppy)$_2$(dtbbpy)PF$_6$), [4,4'-Bis(1,1-dimethylethyl)-2,2'-bipyridine-κN1,κN1']bis[3,5-difluoro-2-[5-(methyl)-2-pyridinyl-κN]phenyl-κC]Iridium$^{(III)}$ hexafluorophosphate (corresponding to Ir(dF(Me)ppy)$_2$(dtbbpy)PF$_6$), [4,4'-Bis(1,1-dimethylethyl)-2,2'-bipyridine-κN1,κN1']bis[3,5-difluoro-2-[2-pyridinyl-κN]phenyl-κC]Iridium$^{(III)}$ hexafluorophosphate (corresponding to Ir(dFppy)$_2$(dtbbpy)PF$_6$) or [4,4'-Bis(1,1-dimethylethyl)-2,2'-bipyridine-κN1,κN1']bis[3-fluoro-5-trifluoromethyl-2-[5-(trifluoromethyl)-2-pyridinyl-κN]phenyl-κC]Iridium$^{(III)}$ hexafluorophosphate (corresponding to Ir(FCF$_3$(CF$_3$)ppy)$_2$(dtbbpy)PF$_6$). Preferably, the photoredox catalyst may be [4,4'-Bis(1,1-dimethylethyl)-2,2'-bipyridine-κN1,κN1']bis[3,5-difluoro-2-[5-(trifluoromethyl)-2-pyridinyl-κN]phenyl-κC]Iridium$^{(III)}$ hexafluorophosphate.

According to any one of the above embodiments, the photoredox catalyst can be added into the reaction medium of the invention's process in a large range of concentrations. As non-limiting examples, one can cite as photoredox catalyst concentration values those ranging from about 0.01 mol % to about 10 mol %, relative to the amount of the aldehyde, preferably from about 0.05 mol % to about 5 mol %, relative to the amount of the aldehyde, even more preferably, from about 0.1 mol % to about 1 mol %, relative to the amount of the aldehyde. The optimum concentration of the catalyst will depend, as the person skilled in the art knows, on the nature of the latter, on the nature of the aldehyde, the olefin, the hydrogen atom transfer donor and/or the secondary amine, on the reaction temperature as well as on the desired time of reaction.

According to any one of the above embodiments, the hydrogen atom transfer donor may be any hydrogen atom transfer donor used in radical chemistry such metal hydride compounds such as tin, silicon, sulfur, selenium, boron or phosphorous derivatives or organic compounds such as malonitrile.

According to a particular embodiment, the hydrogen atom transfer donor is a sulfur derivative. Preferably, the hydrogen atom transfer donor is a thiophenol of formula

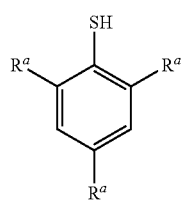

(V)

wherein each $R^a$ represents, independently from each other, a hydrogen atom, a halogen atom, a $C_{1-2}$ linear alkyl group, a $C_{3-4}$ linear or branched alkyl group, a phenyl group optionally substituted by one to five halogen atoms and/or $C_{1-4}$ alkyl or alkoxyl groups or a silyl group trisubstituted with $C_{1-4}$ alkyl groups or an aryl groups; provided that at most two $R^a$ group represent an hydrogen atom. Preferably, the thiophenol may be selected from the group consisting of 2,4,6-trimethylbenzenethiol, 2,4,6-tri-iso-propylbenzenethiol, 2,6-dimethylbenzenethiol, 2,6-di-tert-butyl-4-methylbenzenethiol, 2,6-diisopropylbenzenethiol, 2,4,6-tri-tert-butylbenzenethiol, 4-tert-butylbenzenethiol and 4-fluorobenzenethiol. Preferably, the thiophenol may be selected from the group consisting of 2,4,6-trimethylbenzenethiol, 2,4,6-tri-isopropylbenzenethiol, 2,6-dimethylbenzenethiol, 2,4,6-tri-tert-butylbenzenethiol, 4-tert-butylbenzenethiol and 4-fluorobenzenethiol. Preferably, the thiophenol may be selected from the group consisting of 2,6-dimethylbenzenethiol, 2,4,6-trimethylbenzenethiol, 2,6-di-tert-butyl-4-methylbenzenethiol, 2,6-diisopropylbenzenethiol, 2,4,6-tri-iso-propylbenzenthiol and 2,4,6-tri-tert-butylbenzenthiol Even more preferably, the thiophenol may be 2,4,6-tri-iso-propylbenzenethiol or 2,4,6-tri-tert-butylbenzenthiol.

According to any one of the above embodiments, the thiophenol can be added into the reaction medium of the invention's process in a large range of concentrations. As non-limiting examples, one can cite as thiophenol concentration values those ranging from about 0.5 mol % to about 20 mol %, relative to the amount of the aldehyde, preferably from about 1 mol % to about 10 mol %, relative to the amount of the aldehyde. The optimum concentration of the thiophenol will depend, as the person skilled in the art knows, on the nature of the latter, on the nature of the aldehyde, the olefin, the photoredox catalyst and/or the secondary amine, on the reaction temperature as well as on the desired time of reaction.

According to any one of the above embodiments, the secondary amine may be a cyclic or acyclic amine optionally substituted by one to three halogen atoms or an acid or ester group. Preferably the secondary amine may be of formula

(VI)

wherein $R^b$ and $R^c$ represent, when taken separately, independently from each other, a $C_{1-4}$ alkyl group optionally substituted by one to three halogen atoms; or $R^b$ and $R^c$ represent, when taken together, a $C_{2-4}$ linear alkanediyl group optionally substituted by an ester or an acid group. Said secondary amine may be in the form of ammonium salt.

Preferably, the secondary amine may be selected from the group consisting of 2-(bis(3,5-bis(trifluoromethyl)phenyl) ((trimethylsilyl)oxy)methyl)pyrrolidine, 2,2,2-trifluoro-N-methylethan-1-amine, 2,2,2-trifluoro-N-methylethan-1-aminium chloride, 2,2,2-trifluoro-N-ethylethan-1-amine, 2,2,2-trifluoro-N-ethylethan-1-aminium chloride, bis(2-chloroethyl)amine, bis(2-chloroethyl)aminium chloride, dimethyl amine and dimethylammonium chloride. Preferably, the secondary amine may be selected from the group consisting of 2-(bis(3,5-bis(trifluoromethyl)phenyl)((trimethylsilyl)oxy)methyl)pyrrolidine, 2,2,2-trifluoro-N-methylethan-1-amine, 2,2,2-trifluoro-N-methylethan-1-aminium chloride, bis(2-chloroethyl)amine, bis(2-chloroethyl)aminium chloride, dimethyl amine and dimethylammonium chloride. Even more preferably, the secondary amine may be 2,2,2-trifluoro-N-ethylethan-1-amine or 2,2,2-trifluoro-N-methylethan-1-amine. Even more preferably, the secondary amine may be 2,2,2-trifluoro-N-methylethan-1-amine. The secondary amine may be also in a form of a salt.

According to any one of the above embodiments, the secondary amine can be added into the reaction medium of the invention's process in a large range of concentrations. As non-limiting examples, one can cite as secondary amine concentration values those ranging from about 0.5 mol % to about 20 mol %, relative to the amount of the aldehyde, preferably from about 5 mol % to about 15 mol %, relative to the amount of the aldehyde. The optimum concentration of the secondary amine will depend, as the person skilled in the art knows, on the nature of the latter, on the nature of the aldehyde, the olefin, the photoredox catalyst and/or the hydrogen atom transfer donor, on the reaction temperature as well as on the desired time of reaction.

According to any one of the above embodiments, the light may have a wavelength comprised in the range between 250 nm and 800 nm. Preferably, the light may be UV visible light. Said light may be generated by LED lamp or LED strip.

According to any one of the above embodiments, the invention's process may optionally be carried out in the presence of an inorganic or organic acid such as hydrochloric acid, trifluoroacetic acid or para toluene sulfonic acid.

The reaction can be carried out in the presence or absence of a solvent. When a solvent is required or used for practical reasons, then any solvent current in such reaction type can be used for the purposes of the invention. Solvents with high dielectric constant are preferred. Non-limiting examples of solvents include DMSO, DMPU, DMF, DMA, NMP, acetonitrile, DME, methyl tetrahydrofuran or mixtures thereof. The choice of the solvent is function of the nature of the substrates and/or catalyst and the person skilled in the art is well able to select the solvent most suitable in each case to optimize the reaction.

The invention's process can be carried out at a temperature in the range comprised between 0° C. and 50° C., more. Preferably, the invention's process can be carried out at room temperature; i.e. around 25° C. Of course, a person skilled in the art is also able to select the preferred temperature according to the melting and boiling point of the starting and final products as well as the desired time of reaction or conversion.

The invention's process can be carried out under batch or continuous conditions.

Surprisingly, the invention's process allows avoiding the formation of the ketone side product also known as Kharasch ketone which is formed in a standard radical process. In other words, the invention's process provides a compound or a mixture of compounds free of Kharasch ketone. Without be bound by theory, the invention's process, providing a compound of formula (I), could be divided into several steps; i.e. the reaction of the secondary amine with the aldehyde forming an enamine, then the formation of an enaminyl radical, the addition of the olefin compound with said radical, the opening of the strained cycle and finally the trapping of the radical with the hydrogen atom transfer donor. However, a part of the radical intermediate specie may be partly trapped before the ring opening step of this process leading to the formation of a secondary product in addition to compound of formula (I).

So, according to any one of the above embodiments, the invention's process may provide, in addition, compound of formula (I), a secondary product of formula

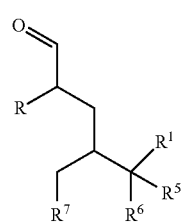

(VII)

in the form of any one of its stereoisomers or a mixture thereof; and wherein R represents a hydrogen atom or a $C_{1-8}$ linear alkyl group; $R^1$ represents a hydrogen atom or a $C_{1-2}$ linear alkyl group or a $C_{3-4}$ linear or branched alkyl group; and $R^5$, $R^6$ and $R^7$ are taken together and represent a $C_{4-12}$ linear, branched or alicyclic alkanetryil.

According to any one of the above embodiments, compound of formula (VII) does not comprise a fused cyclopropyl ring.

According to any one of the above embodiments, the secondary product may be a compound of formula

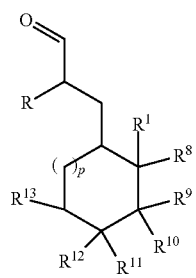

(VIII)

in the form of any one of its stereoisomers or a mixture thereof; and wherein p is 0 or 1; R represents a hydrogen atom or a $C_{1-8}$ linear alkyl group; $R^1$, $R^9$, $R^{10}$, $R^{11}$ $R^{12}$ and $R^{13}$ represent, when taken separately, independently from each other, a hydrogen atom or a $C_{1-2}$ linear alkyl group or a $C_{3-5}$ linear or branched alkyl group; or $R^8$ and $R^9$ represent, when taken together, a $C_2$ linear alkanediyl group or a $C_{3-4}$ linear or branched alkanediyl group; or $R^8$ and $R^{11}$ represent, when taken together, a $C_{1-2}$ linear alkanediyl group or a $C_{3-4}$ linear or branched alkanediyl group; or $R^8$ and $R^{13}$ represent, when taken together, a $C_{1-2}$ linear alkanediyl group or a $C_{3-4}$ linear or branched alkanediyl group; or $R^8$, $R^{11}$ and $R^{12}$ represent, when taken together, a $C_{3-10}$ linear or branched alkanetriyl group; provided that $R^8$ and $R^9$ or $R^8$ and $R^{11}$ or $R^8$ and $R^{13}$ or $R^8$, $R^{11}$ and $R^{12}$ are taken together. When $R^8$ and $R^9$ are taken together, the ring has to be different than a cyclopropyl ring.

According to a particular embodiment, the secondary product may be a compound of formula

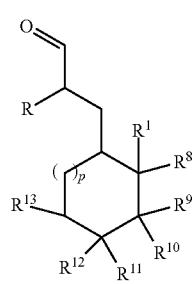

(VIII)

in the form of any one of its stereoisomers or a mixture thereof; and wherein p is 0 or 1; R represents a hydrogen atom or a $C_{1-8}$ linear alkyl group; $R^1$, $R^9$, $R^{10}$, $R^{11}$ $R^{12}$ and $R^{13}$ represent, when taken separately, independently from each other, a hydrogen atom or a $C_{1-2}$ linear alkyl group or a $C_{3-5}$ linear or branched alkyl group; or $R^8$ and $R^{11}$ represent, when taken together, a $C_{1-2}$ linear alkanediyl group or a $C_{3-4}$ linear or branched alkanediyl group; or $R^8$ and $R^{13}$ represent, when taken together, a $C_{1-2}$ linear alkanediyl group or a $C_{3-4}$ linear or branched alkanediyl group; or $R^8$, $R^{11}$ and $R^{12}$ represent, when taken together, a $C_{3-10}$ linear or branched alkanetriyl group; provided that $R^8$ and $R^{11}$ or $R^8$ and $R^{13}$ or $R^8$, $R^{11}$ and $R^{12}$ are taken together.

According to a particular embodiment, the secondary product may be a compound of formula

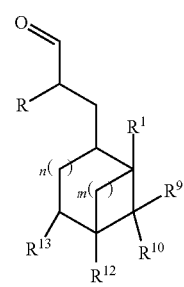

(IX)

in the form of any one of its stereoisomers or a mixture thereof; and wherein R represents a hydrogen atom or a $C_{1-8}$ linear alkyl group; n is an integer between 0 and 1; m is 1 or 2; $R^1$, $R^9$, $R^{10}$, $R^{12}$ and $R^{13}$ represent, when taken separately, independently from each other, a hydrogen atom or a $C_{1-2}$ linear alkyl group or a $C_{3-5}$ linear or branched alkyl.

Non-limiting examples of secondary product may include 3-(6,6-dimethylbicyclo[3.1.1]heptan-2-yl)-2-methylpropanal, and 3-((1S,5S)-6,6-dimethylbicyclo[3.1.1]heptan-2-yl)-2-methylpropanal.

So another object of the present invention is a composition of matter comprising compound of formula (I) and compound of formula (VII). Preferably, the composition of matter comprises compound of formula (I) and compound of formula (VIII). Even more preferably, the composition of matter comprises compound of formula (I) and compound of formula (IX). Even more preferably, the composition of matter comprises 3-(6,6-dimethylbicyclo[3.1.1]heptan-2-yl)-2-methylpropanal and 3-(4-isopropylcyclohex-1-en-1-yl)-2-methylpropanal. Even more preferably, the composition of matter comprises 3-((S)-4-isopropylcyclohex-1-en-1-yl)-2-methylpropanal and 3-((1S,5S)-6,6-dimethylbicyclo[3.1.1]heptan-2-yl)-2-methylpropanal. Said composition of matter can be used as perfuming ingredient, for instance to impart odor notes of the lily of the valley type with a white peach connotation.

Said composition of matter obtainable by the invention's process comprises compound of formula (I) and compound of formula (VII) or of formula (VIII) or of formula (IX) generated from the same starting material.

According to any one of the above embodiments, the composition of matter comprises from 0.1 wt % to 50 wt % of compound of formula (VII), relative to the total weight of the composition. Preferably, the composition of matter may comprise from 0.5 wt % to 30 wt % of compound of formula (VII), relative to the total weight of the composition. Even more preferably, the composition of matter may comprise from 0.5 wt % to 20 wt % of compound of formula (VII), relative to the total weight of the composition. Even more preferably, the composition of matter may comprise from 0.5 wt % to 10 wt % of compound of formula (VII), relative to the total weight of the composition. Even more preferably, the composition of matter may comprise from 1 wt % to 5 wt % of compound of formula (VII), relative to the total weight of the composition. In addition the composition of matter comprised less than 0.1 wt % of Kharasch ketone. Preferably, the composition of matter is free of Kharasch ketone. The presence of said ketone has to be avoided in the composition of matter as it is detrimental to the organoleptic note of the composition of matter. Said ketone imparts a note of the fatty, oil, nutty and rancid type which is perceived even at very low amount; i.e even at 0.1 wt %.

As a specific example of the invention's composition of matter, one may cite, a composition comprising 3-((S)-4-isopropylcyclohex-1-en-1-yl)-2-methylpropanal and 3-((1S,5S)-6,6-dimethylbicyclo[3.1.1]heptan-2-yl)-2-methylpropanal in a respective molar ratio of 94:6 which has a powerful lily of the valley and watery odor typical of the Lilial® comprising some hesperidia and lactonic white peach twist which is a rare combination for perfumery ingredients. Said composition of matter is characterized by an odor having lily of the valley and watery notes duality as Lilial®, comprising also petaly and velvety connotations. The isomer 3-((R)-4-isopropylcyclohex-1-en-1-yl)-2-methylpropanal is less powerful and possesses an aldehydic-metallic top note whereas the floral aspect with the watery and lily of the valley duality is less present which make it less interesting in an organoleptic point of view. Moreover, a mixture comprising 3-((S)-4-isopropylcyclohex-1-en-1-yl)-2-methylpropanal and 3-((R)-4-isopropylcyclohex-1-en-1-yl)-2-methylpropanal in a 1 to 1 ratio, which should correspond to 3-(4-isopropylcyclohex-1-en-1-yl)-2-methylpropanal disclosed US 2013/0090390, is less strong and diffusive that the invention's composition of matter and loses its freshness and its cyclamen florally becoming more fatty-aldehydic and metallic.

When the odor of the invention's composition of matter is compared with that of the prior art compound, i.e. 3-(4-isopropylcyclohex-1-en-1-yl)-2-methylpropanal as reported in US 2013/0090390, the invention's composition of matter distinguishes themselves by a clearly more powerful and diffusive note having a water melon odor and a characteristic lactonic aspect reminiscent of the white peach and by lacking the aldehydic note characteristic of the prior art compound(s). Moreover the invention's composition of matter, contrary to the prior art, besides a lily of the valley—watery note, shows an odor that is allied with a texture of peach skin such as velvety and petali. The odors of the invention's composition of matter are also lacking, or not possessing significant sweet notes which are characteristic of the prior art compounds. Said differences lend the invention's composition of matter and the prior art compound to be each suitable for different uses, i.e. to impart different organoleptic impressions.

As mentioned above, the invention concerns the use of a composition of matter comprising compound of formula (I) and compound of formula (VII). So, another object of the present invention is the use of a composition of matter comprising compound of formula (I) and compound of formula (VII) as a perfuming ingredient. In other words, it concerns a method or a process to confer, enhance, improve or modify the odor properties of a perfuming composition or of a perfumed article or of a surface, which method comprises adding to said composition or article an effective amount of at least composition of matter comprising compound of formula (I) and compound of formula (VII) preferably of formula (VIII), even more preferably of formula (IX), e.g. to impart its typical note.

By "use of a composition of matter" or similar, it has to be understood here also the use of any composition containing a mixture of compound (I) and compound (VII) and which can be advantageously employed in the perfumery industry.

Said compositions, which in fact can be advantageously employed as perfuming ingredients, are also an object of the present invention.

Therefore, another object of the present invention is a perfuming composition comprising:
i) as a perfuming ingredient, at least one invention's composition of matter as defined above;
ii) at least one ingredient selected from the group consisting of a perfumery carrier and a perfumery base; and
iii) optionally at least one perfumery adjuvant.

By "perfumery carrier" it is meant a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as butylene or propylene glycol, glycerol, dipropyleneglycol and its monoether, 1,2,3-propanetriyl triacetate, dimethyl glutarate, dimethyl adipate 1,3-diacetyloxypropan-2-yl acetate, diethyl phthalate, isopropyl myristate, benzyl benzoate, benzyl alcohol, 2-(2-ethoxyethoxy)-1-ethano, tri-ethyl citrate or mixtures thereof, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company), or hydrogenated castors oils such as those known under the trademark Cremophor® RH 40 (origin: BASF).

Solid carrier is meant to designate a material to which the perfuming composition or some element of the perfuming composition can be chemically or physically bound. In general such solid carriers are employed either to stabilize the composition, or to control the rate of evaporation of the compositions or of some ingredients. The use of solid carrier is of current use in the art and a person skilled in the art knows how to reach the desired effect. However by way of non-limiting example of solid carriers, one may cite absorbing gums or polymers or inorganic materials, such as porous polymers, cyclodextrines, wood based materials, organic or inorganic gels, clays, gypsum talc or zeolites.

As other non-limiting examples of solid carriers, one may cite encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs-und Geliermittel in Lebensmitteln, Band 2 der Schriftenreihe Lebensmittelchemie, Lebensmittelqualitat, Behr's Verlag GmbH & Co., Hamburg, 1996. The encapsulation is a well-known process to a person skilled in the art, and may be performed, for instance, by using techniques such as spray-drying, agglomeration or yet extrusion; or consists of a coating encapsulation, including coacervation and complex coacervation technique.

As other non-limiting examples of solid carriers, one may cite in particular the core-shell capsules with resins of aminoplast, polyamide, polyester, polyurea or polyurethane type or a mixture thereof (all of said resins are well known to a person skilled in the art) using techniques like phase separation process induced by polymerization, interfacial polymerization, coacervation or altogether (all of said techniques have been described in the prior art), optionally in the presence of a polymeric stabilizer or of a cationic copolymer.

Resins may be produced by the polycondensation of an aldehyde (e.g. formaldehyde, 2,2-dimethoxyethanal, glyoxal, glyoxylic acid or glycolaldehyde and mixtures thereof) with an amine, such as urea, benzoguanamine, glycoluryl, melamine, methylol melamine, methylated methylol melamine, guanazole and the like, as well as mixtures thereof. Alternatively one may use preformed resins alkylolated polyamines such as those commercially available under the trademark Urac® (origin: Cytec Technology Corp.), Cymel® (origin: Cytec Technology Corp.), Urecoll® or Luracoll® (origin: BASF).

Others resins are the ones produced by the polycondensation of an a polyol, like glycerol, and a polyisocyanate, like a trimer of hexamethylene diisocyanate, a trimer of isophorone diisocyanate or xylylene diisocyanate or a Biuret of hexamethylene diisocyanate or a trimer of xylylene diisocyanate with trimethylolpropane (known with the tradename of Takenate®, origin: Mitsui Chemicals), among which a trimer of xylylene diisocyanate with trimethylolpropane and a Biuret of hexamethylene diisocyanate.

Some of the seminal literature related to the encapsulation of perfumes by polycondensation of amino resins, namely melamine based resins with aldehydes includes articles such as those published by K. Dietrich et al. in Acta Polymerica 1989, vol. 40, pages 243, 325 and 683, as well as 1990, vol. 41, page 91. Such articles already describe the various parameters affecting the preparation of such core-shell microcapsules following prior art methods that are also further detailed and exemplified in the patent literature. U.S. Pat. No. 4,396,670, to the Wiggins Teape Group Limited is a pertinent early example of the latter. Since then, many other authors have enriched the literature in this field and it would be impossible to cover all published developments here, but the general knowledge in encapsulation technology is very significant. More recent publications of pertinency, which disclose suitable uses of such microcapsules, are represented for example by the article of H. Y. Lee et al. in Journal of Microencapsulation, 2002, vol. 19, pages 559-569, international patent publication WO 01/41915 or yet the article of S. Bone et al. in Chimia, 2011, vol. 65, pages 177-181.

By "perfumery base", what is meant here is a composition comprising at least one perfuming co-ingredient.

Said perfuming co-ingredient is not of formula (I) or of formula (VII). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin.

In particular one may cite perfuming co-ingredients which are commonly used in perfume formulations, such as:
  Aldehydic ingredients: decanal, dodecanal, 2-methyl-undecanal, 10-undecenal, octanal and/or nonenal;
  Aromatic-herbal ingredients: *Eucalyptus* oil, camphor, eucalyptol, menthol and/or alpha-pinene;
  Balsamic ingredients: coumarine, ethylvanillin and/or vanillin;
  Citrus ingredients: dihydromyrcenol, citral, orange oil, linalyl acetate, citronellyl nitrile, orange terpenes, limonene, 1-P-menthen-8-yl acetate and/or 1,4(8)-P-menthadiene;
  Floral ingredients: Methyl dihydrojasmonate, linalool, Citronellol, phenylethanol, 3-(4-tert-butylphenyl)-2-methylpropanal, hexylcinnamic aldehyde, benzyl acetate, benzyl salicylate, tetrahydro-2-isobutyl-4-methyl-4(2H)-pyranol, beta ionone, methyl 2-(methylamino)benzoate, (E)-3-methyl-4-(2,6,6-trimethyl-2-cyclohexen-1-yl)-3-buten-2-one, hexyl salicylate, 3,7-dimethyl-1,6-nonadien-3-ol, 3-(4-isopropylphenyl)-2-methylpropanal, verdyl acetate, geraniol, P-menth-1-en-8-ol, 4-(1,1-dimethylethyl)-1-cyclohexyl acetate, 1,1-dimethyl-2-phenylethyl acetate, 4-cyclohexyl-2- methyl-2-butanol, amyl salicylate, high cis methyl dihydrojasmonate, 3-methyl-5-phenyl-1-pentanol, verdyl proprionate, geranyl acetate, tetrahydro linalool, cis-7-P-methanol, Propyl (S)-2-(1,1-dimethylpropoxy) propanoate, 2-methoxynaphthalene, 2,2,2-trichloro-1-phenylethyl acetate, 4/3-(4-hydroxy-4-methylpentyl)-3-cyclohexene-1-carbaldehyde, amylcinnamic aldehyde, 4-phenyl-2-butanone, isononyl acetate, 4-(1,1-diméthyléthyl)-1-cyclohexyl acetate, verdyl isobutyrate and/or mixture of methylionones isomers;

Fruity ingredients: gamma undecalactone, 4-decanolide, ethyl 2-methyl-pentanoate, hexyl acetate, ethyl 2-methylbutanoate, gamma nonalactone, allyl heptanoate, 2-phenoxyethyl isobutyrate, ethyl 2-methyl-1,3-dioxolane-2-acetate and/or diethyl 1,4-cyclohexane dicarboxylate;

Green ingredients: 2,4-Dimethyl-3-cyclohexene-1-carbaldehyde, 2-tert-butyl-1-cyclohexyl acetate, styrallyl acetate, allyl (2-methylbutoxy)acetate, 4-methyl-3-decen-5-ol, diphenyl ether, (Z)-3-hexen-1-ol and/or 1-(5,5-dimethyl-1-cyclohexen-1-yl)-4-penten-1-one;

Musk ingredients: 1,4-dioxa-5,17-cycloheptadecanedione, pentadecenolide, 3-Methyl-5-cyclopentadecen-1-one, 1,3,4,6,7,8-hexahydro-4,6,6,7,8,8-hexamethyl-cyclopenta-g-2-benzopyrane, (1S,1'R)-2-[1-(3',3'-dimethyl-r-cyclohexyl)ethoxy]-2-methylpropyl propanoate, pentadecanolide and/or (1S,1'R)-[1-(3',3'-Dimethyl-r-cyclohexyl)ethoxycarbonyl]methyl propanoate;

Woody ingredients: 1-(octahydro-2,3,8,8-tetramethyl-2-naphtalenyl)-1-ethanone, patchouli oil, terpenes fractions of patchouli oil, (1'R,E)-2-ethyl-4-(2',2',3'-trimethyl-3'-cyclopenten-1'-yl)-2-buten-1-ol, 2-ethyl-4-(2,2,3-trimethyl-3-cyclopenten-1-yl)-2-buten-1-ol, Methyl cedryl ketone, 5-(2,2,3-trimethyl-3-cyclopentenyl)-3-methylpentan-2-ol, 1-(2,3,8,8-tetramethyl-1,2,3,4,6,7,8,8a-octahydronaphthalen-2-yl)ethan-1-one and/or isobornyl acetate;

Other ingredients (e.g. amber, powdery spicy or watery): dodecahydro-3a,6,6,9a-tetramethyl-naphtho[2,1-b]furan and any of its stereoisomers, heliotropin, anisic aldehyde, eugenol, cinnamic aldehyde, clove oil, 3-(1,3-benzodioxol-5-yl)-2-methylpropanal and/or 3-(3-isopropyl-1-phenyl)butanal.

A perfumery base according to the invention may not be limited to the above mentioned perfuming co-ingredients, and many other of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" it is meant here an ingredient capable of imparting additional added benefit such as a color, a particular light resistance, chemical stability, etc. A detailed description of the nature and type of adjuvant commonly used in perfuming composition cannot be exhaustive, but it has to be mentioned that said ingredients are well known to a person skilled in the art. One may cite as specific non-limiting examples the following: viscosity agents (e.g. surfactants, thickeners, gelling and/or rheology modifiers), stabilizing agents (e.g. preservatives, antioxidant, heat/light and or buffers or chelating agents, such as BHT), coloring agents (e.g. dyes and/or pigments), preservatives (e.g. antibacterial or antimicrobial or antifungi or anti irritant agents), abrasives, skin cooling agents, fixatives, insect repellents, ointments, vitamins and mixtures thereof.

It is understood that a person skilled in the art is perfectly able to design optimal formulations for the desired effect by admixing the above mentioned components of a perfuming composition, simply by applying the standard knowledge of the art as well as by trial and error methodologies.

An invention's composition consisting of at least an invention's composition of matter and at least one perfumery carrier consists of a particular embodiment of the invention as well as a perfuming composition comprising at least one invention's composition of matter; i.e. at least one compound of formula (I) and at least one compound of formula (VII), at least one perfumery carrier, at least one perfumery base, and optionally at least one perfumery adjuvant.

According to a particular embodiment, the compositions mentioned above comprise more than one compound of formula (I) and more than one compound of formula (VII) and enable the perfumer to prepare accords or perfumes possessing the odor tonality of various compositions of matter of the invention, creating thus new building block for creation purposes.

For the sake of clarity, it is also understood that any mixture resulting directly from a chemical synthesis, e.g. a reaction medium without an adequate purification, in which the invention's composition of matter would be involved as a starting, intermediate or end-product could not be considered as a perfuming composition according to the invention as far as said mixture does not provide the inventive composition of matter in a suitable form for perfumery. Thus, unpurified reaction mixtures are generally excluded from the present invention unless otherwise specified.

The invention's composition of matter can also be advantageously used in all the fields of modern perfumery, i.e. fine or functional perfumery, to positively impart or modify the odor of a consumer product into which said mixture comprising compound (I) and compound (VII) is added. Consequently, another object of the present invention consists of a perfumed consumer product comprising, as a perfuming ingredient, at least one invention's composition of matter, as defined above.

The invention's composition of matter can be added as such or as part of an invention's perfuming composition.

For the sake of clarity, "perfumed consumer product" is meant to designate a consumer product which delivers at least a pleasant perfuming effect to the surface or space to which it is applied (e.g. skin, hair, textile, or home surface). In other words, a perfumed consumer product according to the invention is a perfumed consumer product which comprises a functional formulation, as well as optionally additional benefit agents, corresponding to the desired consumer product and an olfactive effective amount of at least one invention's composition of matter. For the sake of clarity, said perfumed consumer product is a non-edible product.

The nature and type of the constituents of the perfumed consumer product do not warrant a more detailed description here, which in any case would not be exhaustive, the skilled person being able to select them on the basis of his general knowledge and according to the nature and the desired effect of said product.

Non-limiting examples of suitable perfumed consumer product include a perfume, such as a fine perfume, a splash or eau de parfum, a cologne or a shave or after-shave lotion; a fabric care product, such as a liquid or solid detergent, a fabric softener, a liquid or solid scent booster, a fabric refresher, an ironing water, a paper, a bleach, a carpet cleaner, a curtain-care product; a body-care product, such as a hair care product (e.g. a shampoo, a coloring preparation or a hair spray, a color care product, a hair shaping product, a dental care product), a disinfectant, an intimate care product; a cosmetic preparation (e.g. a skin cream or lotion, a vanishing cream or a deodorant or antiperspirant (e.g. a spray or roll on), a hair remover, a tanning or sun or after sun product, a nail product, a skin cleansing, a makeup); or a skin-care product (e.g. a soap, a shower or bath mousse, oil or gel, or a hygiene product or a foot/hand care products); an air care product, such as an air freshener or a "ready to use" powdered air freshener which can be used in the home space (rooms, refrigerators, cupboards, shoes or car) and/or in a public space (halls, hotels, malls, etc.); or a home care product, such as a mold remover, a furnisher care, a wipe, a dish detergent or a hard-surface (e.g. a floor, bath, sanitary or a windows) detergent; a leather care product; a car care product, such as a polish, a wax or a plastic cleaner.

Some of the above-mentioned perfumed consumer products may represent an aggressive medium for the invention's composition of matter, so that it may be necessary to protect the latter from premature decomposition, for example by encapsulation or by chemically binding it to another chemical which is suitable to release the invention's ingredient upon a suitable external stimulus, such as an enzyme, light, heat or a change of pH.

The proportions in which the composition of matter according to the invention can be incorporated into the various aforementioned products or compositions vary within a wide range of values. These values are dependent on the nature of the article to be perfumed and on the desired organoleptic effect as well as on the nature of the co-ingredients in a given base when the compounds according to the invention are mixed with perfuming co-ingredients, solvents or additives commonly used in the art.

For example, in the case of perfuming compositions, typical concentrations are in the order of 0.001% to 10% by weight, or even more, of the composition of matter of the invention based on the weight of the composition into which they are incorporated. In the case of perfumed consumer product, typical concentrations are in the order of 0.0001% to 1% by weight, or even more, of the invention's composition of matter based on the weight of the consumer product into which they are incorporated.

Compound of formula (VII) is novel. So another object of the present invention is compound of formula (VII) as defined above. Preferably, the compound of formula (VII) is a compound of formula (VIII) as defined above. Even more preferably, the compound of formula (VII) is a compound of formula (IX) as defined above. As non-limiting examples of the invention's compound, one can cite 3-(6,6-dimethylbi-cyclo[3.1.1]heptan-2-yl)-2-methylpropanal in a form of any-one of its stereoisomers.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 400 or 500 MHz machine for H and C, the chemical shifts δ are indicated in ppm with respect to TMS as standard, the coupling constants J are expressed in Hz.

Example 1

Preparation of 3-((S)-4-isopropylcyclohex-1-en-1-yl)-2-methylpropanal Using the Invention's Process A glass tube with water jacket was charged with (1S,5S)-6,6-dimethyl-2-methylenebicyclo[3.1.1]heptane (2.35 ml, 15 mmol), [4,4CBA(1,1-dimethylethyl)-2,2'-bipyridine-N1,N1']bis[3,5-difluoro-2-[5-(trifluoromethyl)-2-pyridinyl-N]phenyl-C]Iridium$^{(III)}$ hexafluorophosphate (0.0056 g, 0.005 mmol), 2,4,6-tri-tert-butylbenzenethiol (0.037 g, 0.135 mmol), HCl (0.042 ml, 0.25 mmol), $H_2O$ (0.27 ml, 15 mmol), DME (2.5 mL). Finally propionaldehyde (0.366 ml, 5 mmol) and 2,2,2-trifluoro-N-methylethanamine (0.057 g, 0.5 mmol) were added. The mixture was stirred at RT and placed under Blue LED lamp for 24 h. The aqueous layer was taken off, diethylether was added and the organic phase was washed twice with water, dried over magnesium sulfate, and the solvent was evaporated. The crude product was purified by column chromatography (heptane/EtOAc 60/1 as eluent) and then by distillation (0.5 mbar, 120° C.) to afford the desired aldehyde as a colorless oil (0.701 g, 3.57 mmol, 70% yield).

$^1$H NMR ($CDCl_3$, 500 MHz), mixture of two diastereoisomers (1:1): 0.879 (t, J=6.6 Hz, 6H), 0.881 (t, 7=6.5 Hz, t), 1.03 (d, 7=2.3 Hz, 2H), 1.05 (d, J=2.3 Hz, 2H), 1.15-1.28 (m, 4H), 1.42-1.50 (m, 2H), 1.68-1.80 (m, 4H), 1.88-2.07 (m, 10H), 2.33-2.41 (m, 2H), 2.47-2.54 (m, 2H), 5.42-5.46 (m, 2H), 9.61 (d, J=1.9 Hz, 1H), 9.62 (d, J=2.2 Hz, 1H).

$^{13}$C NMR ($CDCl_3$, 125 MHz), mixture of two diastereoisomers (1:1): 205.37 (CH), 205.35 (CH), 134.06 (C), 134.01 (C), 123.92 (CH), 123.86 (CH), 44.43 (CH), 44.34 (CH), 40.06 (CH), 40.01 (CH), 38.87 (CH2), 38.86 (CH2), 32.23 (CH), 32.20 (CH), 28.99 (CH2), 28.95 (CH2), 26.40 (CH2), 26.30 (CH2), 19.96 (CH3), 19.67 (CH3), 13.44 (CH3), 13.17 (CH3).

Example 2

Preparation of a Mixture of 3-((S)-4-isopropylcy-clohex-1-en-1-yl)-2-methylpropanal and 3-((1S, 5S)-6,6-dimethylbicyclo[3.1.1]heptan-2-yl)-2-methylpropanal in a 83/17 Ratio Using the Invention's Process A glass tube with water jacket was charged with (1S,5S)-6,6-dimethyl-2-methylenebicyclo[3.1.1]heptane (23.46 ml, 150 mmol), [4,4'-Bis(1,1-dimethylethyl)-2,2'-bipyridine-N1,N1']bis[3,5-difluoro-2-[5-(trifluoromethyl)-2-pyridinyl-N]phenyl-C]Iridium$^{(III)}$ hexafluorophosphate (0.057 g, 0.051 mmol), 2,4,6-tri-iso-isopropylbenzenethiol (0.297 g, 1.256 mmol), HCl (0.417 ml, 2.50 mmol), $H_2O$ (2.7 ml, 150 mmol), DME (25 mL). Finally propionaldehyde (3.59 ml, 50.0 mmol) and 2,2,2-trifluoro-N-methylethanamine (0.571 g, 5.05 mmol) were added. The mixture was stirred at RT and placed under Blue LED lamp for 24 h. The aqueous layer was taken off, diethylether was added and the organic phase was washed twice with water, dried over magnesium sulfate, and the solvent was evaporated. The crude product was purified by distillation (0.5 mbar, 120° C.) to afford the desired mixture of aldehydes (i.e. 3-((.V)-4-isopropylcyclo-hex-1-en-1-yl)-2-methylpropanal and 3-((1S,5S)-6,6-dim-ethylbicyclo[3.1.1]heptan-2-yl)-2-methylpropanal) as color-less oil (8.244 g, 40.7 mmol, 81% yield, ratio 83/17). Spectral data of 3-((S)-4-isopropylcyclohex-1-en-1-yl)-2-methylpropanal were described in example 1.

3-((1S,2R,5S)-6,6-dimethylbicyclo[3.1.1]heptan-2-yl)-2-methylpropanal $^1$H NMR (C$_6$D$_6$, 500 MHz): 0.72 (s, 3H), 0.73 (s, 3H), 0.78 (d, J=9.0 Hz, 3H), 0.79 (d, J=9.0 Hz, 3H), 0.84-1.07 (m, 4H), 1.16 (s, 6H), 1.21 (dd, J=2.1, 10.1 Hz, 2H), 1.35-1.51 (m, 4H), 1.53-1.56 (m, 2H), 1.60-1.73 (m, 4H), 1.78-1.82 (m, 2H), 1.83-1.90 (m, 2H), 1.92-2.01 (m, 4H), 9.310 (d, J=2.3 Hz, 1H), 9.315 (d, J=2.0 Hz, 1H).

$^{13}$C NMR (C$_6$D$_6$, 125 MHz): 203.50 (CH), 203.48 (CH), 46.27 (CH), 45.65 (CH), 43.84 (CH), 41.27 (CH), 41.23 (CH), 39.56 (C), 39.46 (C), 37.49 (CH2), 37.23 (CH2), 32.24 (CH), 32.07 (CH), 26.92 (CH3), 26.89 (CH3), 24.74 (CH2), 24.69 (CH2), 23.60 (CH2), 23.43 (CH2), 22.77 (CH2), 22.14 (CH2), 20.05 (CH3), 14.04 (CH3), 13.37 (CH3).

3-((1S,2S,5S)-6,6-dimethylbicyclo[3.1.1]heptan-2-yl)-2-methylpropanal $^1$H NMR (CDCl$_3$, 500 MHz): 1.02 (s, 6H), 1.067 (d, J=7.0 Hz, 3H), 1.071 (d, J=6.9 Hz, 3H), 1.185 (s, 3H), 1.190 (s, 3H), 1.32-1.52 (m, 4H), 1.80-1.99 (m, 12H), 2.00-2.13 (m, 4H), 2.30-2.44 (m, 4H), 9.58 (d, J=2.5 Hz, 1H), 9.60 (d, J=2.1 Hz, 1H).

$^{13}$C NMR (CDCl$_3$, 125 MHz): 205.57 (CH), 205.51 (CH), 46.58 (CH), 45.98 (CH), 44.76 (CH), 44.69 (CH), 41.42 (CH), 41.39 (CH), 38.72 (CH), 38.70 (C), 38.67 (CH2), 38.42 (CH), 38.28 (CH2), 33.78 (CH2), 33.57 (CH2), 28.16 (CH3), 26.36 (CH2), 23.34 (CH3), 23.31 (CH3), 22.68 (CH2), 22.18 (CH2), 14.07 (CH3), 13.34 (CH3).

Example 3

Preparation of a mixture of 3-((S)-4-isopropylcyclohex-1-en-1-yl)-2-methylpropanal and 3-((1S,5S)-6,6-dimethylbicyclo[3.1.1]heptan-2-yl)-2-methylpropanal in a 94/6 Ratio Using the Invention's Process A flask with water jacket was charged with (1S,5S)-6,6-dimethyl-2-methylenebicyclo[3.1.1]heptane (9.38 ml, 60 mmol), [4,4'-Bis(1,1-dimethylethyl)-2,2'-bipyridine-N1,N1']bis[3,5-difluoro-2-[5-(trifluoromethyl)-2-pyridinyl-N]phenyl-C]Iridium$^{(III)}$ hexafluorophosphate (0.022 g, 0.02 mmol), 2,4,6-tri-tert-butylbenzenethiol (0.278 g, 1.00 mmol), HCl (0.17 ml, 1.00 mmol), H$_2$O (1.1 ml, 60 mmol), DME (10 mL). Finally propionaldehyde (1.45 ml, 20 mmol) and 2,2,2-trifluoro-N-methylethanamine (0.222 g, 1.96 mmol) were added. The mixture was stirred at RT and placed under Blue LED lamp for 24 h. The aqueous layer was taken off, diethylether was added and the organic phase was washed twice with water, dried over magnesium sulfate, and the solvent was evaporated. The crude product was purified by distillation (0.5 mbar, 120° C.) to afford the desired aldehydes (i.e. 3-((S)-4-isopropylcyclohex-1-en-1-yl)-2-methylpropanal and 3-((1S,5S)-6,6-dimethylbicyclo[3.1.1]heptan-2-yl)-2-methylpropanal) as colorless oil (2.78 g, 13.9 mmol, 69% yield, ratio 94/6).

Example 4

Invention's Process Using Different Hydrogen Atom Transfer Donors

Following, the typical procedure as described in Example 1, under these conditions several hydrogen atom transfer donors as reported in Table 1 were tested. The results are reported in Table 1.

TABLE 1

Preparation of 3-((S)-4-isopropylcyclohex-1-en-1-yl)-2-methylpropanal under the invention's process using different hydrogen atom transfer donors

| Hydrogen atom transfert donor | Yield (%) | (I)[1] GC (%) | (IX)[2] GC (%) | Ratio (I)/(XI) | Ketone[3] GC (%) |
|---|---|---|---|---|---|
| 2,6-dimethylbenzenethiol | 63 | 88.4 | 7.4 | 92/8 | not observed |
| 2,4,6-trimethylbenzenethiol | 71 | 85.2 | 9.1 | 90/10 | not observed |
| 2,6-di-tert-butyl-4-methylbenzenethiol | 81 | 86.8 | 3 | 97/3 | not observed |
| 2,6-diisopropylbenzenethiol | 85 | 78.9 | 14.7 | 84/16 | not observed |
| 2,4,6-tri-iso-propylbenzenthiol | 81 | 79.4 | 16.2 | 83/17 | not observed |
| 2,4,6-tri-tert-butylbenzenthiol | 81 | 93.1 | 3 | 97/3 | not observed |

[1] 3-((S)-4-isopropylcyclohex-1-en-1-yl)-2-methylpropanal
[2] 3-((1S,5S)-6,6-dimethylbicyclo[3.1.1]heptan-2-yl)-2-methylpropanal
[3] 1-(4-isopropyl-1-cyclohexen-1-yl)-2-butanone Said results clearly demonstrated that the invention's process allows providing a composition of matter free of the 1-(4-isopropyl-1-cyclohexen-1-yl)-2-butanone corresponding to the Kharasch ketone.

Example 5

Invention's Process Using Different Secondary Amines

Following, the typical procedure as described in Example 1, under these conditions several secondary amines as reported in Table 2 were tested. The results are reported in Table 2.

TABLE 2

Preparation of 3-((S)-4-isopropylcyclohex-1-en-1-yl)-2-methylpropanal under the invention's process using different secondary amines

| Secondary amine | Yield (%) | (I)[1] GC (%) | (IX)[2] GC (%) | Ratio (I)/(XI) | Ketone[3] GC (%) |
|---|---|---|---|---|---|
| 2,2,2-trifluoro-N-methylethan-1-aminium chloride | 72 | 86.4 | 2.7 | 97/3 | not observed |
| 2,2,2-trifluoro-N-methylethan-1-amine | 81 | 93.1 | 3 | 97/3 | not observed |
| 2,2,2-trifluoro-N-ethylethan-1-aminium chloride | 40 | 86.5 | 0.7 | 99/1 | not observed |

[1] 3-((S)-4-isopropylcyclohex-1-en-1-yl)-2-methylpropanal
[2] 3-((1S,5S)-6,6-dimethylbicyclo[3.1.1]heptan-2-yl)-2-methylpropanal
[3] 1-(4-isopropyl-1-cyclohexen-1-yl)-2-butanone Said results clearly demonstrated that the invention's process allows providing a composition of matter free of the 1-(4-isopropyl-1-cyclohexen-1-yl)-2-butanone corresponding to the Kharasch ketone.

Example 6

Invention's Process Using Different Photoredox Catalysts

Following, the typical procedure as described in Example 1, under these conditions several photoredox catalysts as reported in Table 3 were tested. The results are reported in Table 3.

TABLE 3

Preparation of 3-((S)-4-isopropylcyclohex-1-en-1-yl)-2-methylpropanal under the invention's process using different photoredox catalysts

| Photoredox catalysts | Yield (%) | (I)[1] GC (%) | (IX)[2] GC (%) | Ratio (I)/(XI) | Ketone[3] GC (%) |
|---|---|---|---|---|---|
| Ir(dF(CF3)ppy)$_2$(dtbbpy)PF$_6$ | 81 | 93.1 | 3 | 97/3 | not observed |
| Ir(dF(Me)ppy)$_2$(dtbbpy)PF$_6$ | 73 | 91.4 | 1.2 | 99/1 | not observed |
| Ir(dFppy)$_2$(dtbbpy)PF$_6$ | 75 | 88.5 | 1.1 | 99/1 | not observed |
| Ir(FCF$_3$(CF$_3$)PPY)$_2$(dtbbpy)PF$_6$ | 70 | 91.5 | 0.9 | 99/1 | not observed |

[1] 3-((S)-4-isopropylcyclohex-1-en-1-yl)-2-methylpropanal
[2] 3-((1S,5S)-6,6-dimethylbicyclo[3.1.1]heptan-2-yl)-2-methylpropanal
[3] 1-(4-isopropyl-1-cyclohexen-1-yl)-2-butanone Said results clearly demonstrated that the invention's process allows providing a composition of matter free of the 1-(4-isopropyl-1-cyclohexen-1-yl)-2-butanone corresponding to the Kharasch ketone.

Example 7

Preparation of a Perfuming Composition

A perfuming composition for fabric softener was prepared by admixing the following ingredients:

| Parts by weight | Ingredient |
|---|---|
| Benzyl acetate | 600 |
| Carbinol acetate | 100 |
| (Z)-3-hexen-1-ol acetate | 20 |
| Cinnamic alcohol | 100 |
| Anisic aldehyde | 40 |
| C 12 Aldehyde | 10 |
| Hexylcinnamic aldehyde | 1400 |
| Allyl amyl glycolate | 40 |
| Methyl anthranilate | 20 |
| Gamma undecalactone | 100 |
| Nitrile citronellyl | 20 |
| Verdyle acetate | 200 |
| Verdyle propionate | 100 |
| Damascone alpha | 10 |
| Dartanol ® [1] | 140 |
| Dihydromyrcenol | 400 |
| Diphenyl oxyde | 100 |
| Eugenol | 100 |
| Habanolide ® [2] | 1000 |
| Hedione ® [3] | 1000 |
| Phenethylol | 1000 |
| Rosinol[4] | 40 |
| Amyle salicylate | 1200 |
| Terpineol | 1000 |
| Verdox ™ [5] | 200 |
| Ylang essential oil | 60 |
| | 9000 |

[1] (1'R,E)-2-ethyl-4-(2',2',3'-trimethyl-3'-cyclopenten-1'-yl)-2-buten-1-ol; origin: Firmenich S A, Geneva, Switzerland
[2] Pentadecenolide; origin: Firmenich S A, Geneva, Switzerland
[3] Methyl dihydrojasmonate; origin: Firmenich S A, Geneva, Switzerland
[4] 2,2,2-trichloro-1-phenylethyl acetate; origin: Firmenich S A, Geneva, Switzerland
[5] 2-tert-butyl-1-cyclohexyl acetate; origin: International Flavors & Fragrances, USA The addition of 1000 parts by weight of 3-((S)-4-isopropylcyclohex-1-en-1-yl)-2-methylpropanal obtained in example 1 or of a mixture comprising 3-((5')-4-isopropylcyclohex-1-en-1-yl)-2-methylpropanal, 3-((1S,2R,5S)-6,6-dimethylbicyclo[3.1.1]heptan-2-yl)-2-methylpropanal and 3-((1S,2S,5S)-6,6-dimethylbicyclo[3.1.1]heptan-2-yl)-2-methylpropanal as obtained in example 2 to the above-described composition imparted to the latter distinctly fresh cyclamen and lily of the valley connotation and conferred more watery freshness to its top and bottom note. The composition comprising the invention's composition of matter as obtained in example 2 acquires a slightly more aqueous connotation than the composition comprising only 3-((S)-4-isopropylcyclohex-1-en-1-yl)-2-methylpropanal.

When, instead of 3-((S)-4-isopropylcyclohex-1-en-1-yl)-2-methylpropanal or of the invention's composition of matter, the same amount of a mixture comprising 3-((S)-4-isopropylcyclohex-1-en-1-yl)-2-methylpropanal and 1-(4-isopropyl-1-cyclohexen-1-yl)-2-butanone (Kharasch ketone) in a respective amount of 99.9 wt % and 0.1 wt %: was used, the composition acquired a fatty and unclean connotation. The composition became clearly less fresh and transparent.

When, instead of 3-((S)-4-isopropylcyclohex-1-en-1-yl)-2-methylpropanal or of the invention's composition of matter, the same amount of 3-((R)-4-isopropylcyclohex-1-en-1-yl)-2-methylpropanal was used, the composition acquired a slightly more fatty-aldehydic but also a more metallic connotation. The effect observed is rather weak and not positive.

When instead of 3-((S)-4-isopropylcyclohex-1-en-1-yl)-2-methylpropanal or of the invention's composition of matter, the same amount of Mugoxal® (3-(4-tert-butyl-1-cyclohexen-1-yl)propanal; origin: Firmenich SA, Geneva, Switzerland) was used, the composition acquired a distinctly elegant and sparkling lily of the valley white flower connotation but devoid of the lactonic white peach note.

When instead of 3-((S)-4-isopropylcyclohex-1-en-1-yl)-2-methylpropanal or of the invention's composition of matter, the same amount of (−)-(S)-3-(4-isopropylcyclohex-1-en-1-yl)propanal reported in US 2013/0090390, was used, the results was totally different as the composition acquired a distinctly clean aldehydic, citrus-lime and mandarine connotation which is classical in this kind of notes. Said compound imparted an aldehydic-citrus note instead of a floral note.

When instead of the 3-((S)-4-isopropylcyclohex-1-en-1-yl)-2-methylpropanal or of the invention's composition of matter was used the same amount of (+−)-2-methyl-3-[4-(2-methyl-2-propanyl)-1-cyclohexen-1-yl]propanal, the composition acquired a lily of the valley connotation reminiscent of Lilial® but devoid of the lactonic white peach note.

Example 8

Preparation of a Fabric Softener Comprising the Invention's Perfuming Composition

TABLE 4

Composition of the softener formulation

| Ingredient | Concentration [wt %] |
|---|---|
| Methyl bis[ethyl (tallowate)]-2-hydroxyethyl ammonium methyl sulfate[1] | 12.20 |
| 1,2-benzisothiazolin-3-one[2] | 0.04 |
| CaCl$_2$ (10% aqueous solution) | 0.40 |
| Water | 87.36 |

[1] Stepantex VL90 A Diester Quat; Origin: Stepan
[2] Proxel GXL; Origin: Arch

The softener was prepared by weighting Methyl bis[ethyl (tallowate)]-2-hydroxyethyl ammonium methyl sulfate which was heated at 65° C. Then Water and 1,2-benzisothiazolin-3-one were placed in the reactor and were heated at 65° C. under stirring. To the above mixture was added Methyl bis[ethyl (tallowate)]-2-hydroxyethyl ammonium methyl sulfate. The mixture was stirred 15 minutes and CaCl$_2$ was added. Then 0.5 to 2% by weight, relative to the total weight of the softener, of the invention's composition of example 7 was added. The mixture was stirred 15 minutes and was cooled down to room temperature under stirring (viscosity measure: result 35+/−5 mPas. (shear rate 106 sec-1)).

Example 9

Preparation of a Liquid Detergent Comprising the Invention's Perfuming Composition

TABLE 5

Composition of the liquid detergent formulation

| Ingredients | Concentration [wt %] |
| --- | --- |
| Sodium C14-17 Alkyl Sec Sulfonate[1] | 7 |
| Fatty acids, C12-18 and C18-unsaturated[2] | 7.5 |
| C12/14 fatty alcohol polyglycol ether with 7 mol EO[3] | 17 |
| Triethanolamine | 7.5 |
| Propylene Glycol | 11 |
| Citric acid | 6.5 |
| Potassium Hydroxyde | 9.5 |
| Properase L[4] | 0.2 |
| Puradax EG L[4] | 0.2 |
| Purastar ST L[4] | 0.2 |
| Acrylates/Steareth-20 Methacrylate structuring Crosspolymer[5] | 6 |
| Deionized Water | 27.4 |

[1]Hostapur SAS 60; Origin: Clariant
[2]Edenor K 12-18; Origin: Cognis
[3]Genapol LA 070; Origin: Clariant
[4]Origin: Genencor International
[5]Aculyn 88; Origin: Dow Chemical The liquid detergent was prepared by adding 0.5 to 1.5% by weight, relative to the total weight of the liquid detergent, of the invention's composition of example 7 into the unperfumed liquid detergent formulation of Table 5 under gentle shaking.

Example 10

Preparation of a Transparent Isotropic Shampoo Comprising the Invention's Perfuming Composition

TABLE 6

Composition of the transparent isotropic shampoo formulation

| Phases | Ingredients | Concentration [wt %] |
| --- | --- | --- |
| A | Water deionized | 44.4 |
| | Polyquaternium-10 [1] | 0.3 |
| | Glycerin 85% [2] | 1 |
| | DMDM Hydantoin [3] | 0.2 |
| B | Sodium Laureth Sulfate [4] | 28 |
| | Cocamidopropyl Betaine [5] | 3.2 |
| | Disodium Cocoamphodiacetate [6] | 4 |
| | Ethoxy (20) Stearyl Alcohol [6] | 1 |
| C | Sodium Laureth Sulfate [4] | 3 |
| | Glyceryl Laureate [7] | 0.2 |
| D | Water deionized | 1 |
| | Sodium Methylparaben [8] | 0.1 |

TABLE 6-continued

Composition of the transparent isotropic shampoo formulation

| Phases | Ingredients | Concentration [wt %] |
| --- | --- | --- |
| E | Sodium Chloride 10% aqueous sol. | 15 |
| | Citric acid 10% aqueous sol. till pH 5.5-6 | q.s. |

[1] Ucare Polymer JR-400, Origin: Noveon
[2] Origin: Schweizerhall
[3] Glydant, Origin: Lonza
[4] Texapon NSO IS, Origin: Cognis
[5] Tego Betain F 50, Origin: Evonik
[6] Amphotensid GB 2009, Origin: Zschimmer & Schwarz
[7] Monomuls 90 L-12, Origin: Gruenau
[8] Nipagin Monosodium, Origin: NIPA The shampoo was prepared by dispersed in water Polyquaternium-10. The remaining ingredients of phase A were mixed separately by addition of one after the other while mixing well after each adjunction. This pre-mix was added to the Polyquaternium-10 dispersion and mixed for another 5 min. Then, the premixed phase B and the premixed Phase C were added (Monomuls 90L-12 was heated to melt in Texapon NSO IS) while agitating. Phase D and Phase E were added while agitating. PH was adjusted with citric acid solution till pH: 5.5-6.0 leading to an unperfumed shampoo formulae.

The perfumed shampoo was prepared by adding 0.4 to 0.8% by weight, relative to the total weight of the shampoo, of the invention's composition of example 7 into the unperfumed shampoo formulation of Table 6 under gentle shaking.

Example 11

Preparation of a Structured Shower Gel Comprising the Invention's Perfuming Composition

TABLE 7

Composition of the shower gel formulation

| Ingredients | Amount (% wt) |
| --- | --- |
| WATER deionised | 49.350 |
| Tetrasodium EDTA [1] | 0.050 |
| Acrylates Copolymer[2] | 6.000 |
| Sodium C12-C15 Pareth Sulfate [3] | 35.000 |
| Sodium Hydroxide 20% aqueous solution | 1.000 |
| Cocamidopropyl Betaine[4] | 8.000 |
| Methylchloroisothiazolinone and Methylisothiazolinone[5] | 0.100 |
| Citric Acid (40%) | 0.500 |

[1] EDETA B POWDER; trademark and origin: BASF
[2]CARBOPOL AQUA SF-1 POLYMER; trademark and origin: NOVEON
[3] ZETESOL AO 328 U; trademark and origin: ZSCHIMMER & SCHWARZ
[4]TEGO-BETAIN F 50; trademark and origin: GOLDSCHMIDT
[5]KATHON CG; trademark and origin: ROHM & HASS The shower gel was prepared by adding 0.5 to 1.5% by weight, relative to the total weight of the shower gel, of the invention's composition of example 7 into the unperfumed shower gel formulation of Table 7 under gentle shaking.

Example 12

Preparation of a Transparent Shower Gel Comprising the Invention's Perfuming Composition

TABLE 8

Composition of the transparent shower gel formulation

| Ingredients | Concentration (% wt) |
|---|---|
| WATER deionized | 52.40 |
| Tetrasodium EDTA [1] | 0.10 |
| Sodium Benzoate | 0.50 |
| Propylene Glycol | 2.00 |
| Sodium C12-C15 Pareth Sulfate [2] | 35.00 |
| Cocamidopropyl Betaine [3] | 8.00 |
| Polyquaternium-7 [4] | 0.20 |
| Citric Acid (40%) | 1.00 |
| Sodium Chloride | 0.80 |

[1] EDETA B POWDER; trademark and origin: BASF
[2] ZETESOL AO 328 U; trademark and origin: ZSCHIMMER & SCHWARZ
[3] TEGO-BETAIN F 50; trademark and origin: GOLDSCHMIDT
[4] MERQUAT 550; trademark and origin: LUBRIZOL The transparent shower gel was prepared by adding 0.5 to 1.5% by weight, relative to the total weight of the shower gel, of the invention's composition of example 7 into the unperfumed shower gel formulation of Table 8 under gentle shaking.

Example 13

Preparation of a Milky Shower Gel Comprising the Invention's Perfuming Composition

TABLE 9

Composition of the milky shower gel formulation

| Ingredients | Concentration (% wt) |
|---|---|
| WATER deionized | 50.950 |
| Tetrasodium EDTA [1] | 0.050 |
| Sodium Benzoate | 0.500 |
| Glycerin 86% | 3.500 |
| Sodium Laureth Sulfate [2] | 27.000 |
| Polyquaternium-7 [3] | 1.000 |
| Coco-Betaine [4] | 6.000 |
| PEG-120 Methyl Glucose trioleate [5] | 1.000 |
| Citric Acid (40%) | 1.000 |
| Glycol Distearate & Laureth-4 & Cocamidopropyl Betaine [6] | 3.000 |
| Sodium Chloride 20% | 5.000 |
| PEG-40 Hydrogenated Castor Oil [7] | 1.000 |

[1] EDETA B POWDER; trademark and origin: BASF
[2] Texapon NSO IS; trademark and origin: COGNIS
[3] MERQUAT 550; trademark and origin: LUBRIZOL
[4] DEHYTON AB-30; trademark and origin: COGNIS
[5] GLUCAMATE LT; trademark and origin: LUBRIZOL
[6] EUPERLAN PK 3000 AM; trademark and origin: COGNIS
[7] CREMOPHOR RH 40; trademark and origin: BASF The transparent shower gel was prepared by adding 0.5 to 1.5% by weight, relative to the total weight of the shower gel, of the invention's composition of example 7 into the unperfumed shower gel formulation of Table 9 under gentle shaking.

Example 14

Preparation of a Pearly Shampoo Comprising the Invention's Perfuming Composition

TABLE 10

Composition of the pearly isotropic shampoo formulation

| Phases | Ingredients | Concentration (% wt) |
|---|---|---|
| A | Water deionized | 45.97 |
|   | Tetrasodium EDTA [1] | 0.05 |
|   | Guar Hydroxypropyltrimonium Chloride [2] | 0.05 |
|   | Polyquaternium-10 [3] | 0.075 |
| B | NaOH 10% aqueous sol. | 0.3 |
| C | Ammonium Lauryl Sulfate [4] | 34 |
|   | Ammonium Laureth Sulfate [5] | 9.25 |
|   | Cocamidopropyl Betaine [6] | 2 |
|   | Dimethicone (&) C12-13 Pareth-4 (&) C12-13 Pareth-23 (&) Salicylic Acid [7] | 2.5 |
| D | Cetyl Alcohol [8] | 1.2 |
|   | Cocamide MEA [9] | 1.5 |
|   | Glycol Distearate [10] | 2 |
| E | Methylchloroisothiazolinone & Methylisothiazolinone [11] | 0.1 |
|   | D-Panthenol 75% [12] | 0.1 |
|   | Water deionized | 0.3 |
| F | Sodium Chloride 25% aqueous sol. | 0.6 |

[1] EDETA B Powder, Origin: BASF
[2] Jaguar C14 S, Origin: Rhodia
[3] Ucare Polymer JR-400, Origin: Noveon
[4] Sulfetal LA B-E, Origin: Zschimmer & Schwarz
[5] Zetesol LA, Origin: Zschimmer & Schwarz
[6] Tego Betain F 50, Origin: Evonik
[7] Xiameter MEM-1691, Origin: Dow Corning
[8] Lanette 16, Origin: BASF
[9] Comperlan 100, Origin: Cognis
[10] Cutina AGS, Origin: Cognis
[11] Kathon CG, Origin: Rohm & Haas
[12] D-Panthenol, Origin: Roche The shampoo was prepared by dispersed in water and Tetrasodium EDTA, Guar Hydroxypropyltrimonium Chloride and Polyquaternium-10. NaOH 10% solution (Phase B) was added once Phase A was homogeneous. Then, the premixed Phase C was added. and mixture was heated to 75° C. Phase D ingredients were added and mixed till homogeneous. The mixture was cooled down. At 45° C., Phase E ingredients were added while mixing. Final viscosity was adjusted with 25% NaCl solution and pH of 5.5-6 was adjusted with 10% NaOH solution.

The perfumed pearly shampoo was prepared by adding 0.4 to 0.8% by weight, relative to the total weight of the shampoo, of the invention's composition of example 7 into the unperfumed shampoo formulation of Table 10 under gentle shaking.

Example 15

Preparation of a Structured Shower Gel Comprising the Invention's Perfuming Composition

TABLE 11

Composition of the milky shower gel formulation

| Ingredients | Amount (% wt) |
|---|---|
| WATER deionised | 49.350 |
| Tetrasodium EDTA [1] | 0.050 |
| Acrylates Copolymer [2] | 6.000 |
| Sodium C12-C15 Pareth | 35.000 |

TABLE 11-continued

| Composition of the milky shower gel formulation | |
|---|---|
| Ingredients | Amount (% wt) |
| Sulfate [3] | |
| Sodium Hydroxide 20% aqueous solution | 1.000 |
| Cocamidopropyl Betaine[4] | 8.000 |
| Methylchloroisothiazolinone and Methylisothiazolinone[5] | 0.100 |
| Citric Acid (40%) | 0.500 |

[1] EDETA B POWDER; trademark and origin: BASF
[2] CARBOPOL AQUA SF-1 POLYMER; trademark and origin: NOVEON
[3] ZETESOL AO 328 U; trademark and origin: ZSCHIMMER & SCHWARZ
[4] TEGO-BETAIN F 50; trademark and origin: GOLDSCHMIDT
[5] KATHON CG; trademark and origin: ROHM & HASS The transparent shower gel was prepared by adding 0.5 to 1.5% by weight, relative to the total weight of the shower gel, of the invention's composition of example 7 into the unperfumed shower gel formulation of Table 11 under gentle shaking.

The invention claimed is:

1. A process for the preparation of a compound of formula

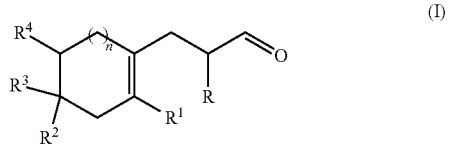

(I)

in a form of any one of its stereoisomers or a mixture thereof and wherein R represents a hydrogen atom or $C_{1-8}$ linear alkyl group; $R^1$, $R^2$, $R^3$ and $R^4$ represent, when taken separately, independently of each other, a hydrogen atom or a $C_{1-2}$ linear alkyl group or a $C_{3-4}$ linear or branched alkyl group; or $R^2$ and $R^3$, when taken together, represent a $C_{4-10}$ linear, branched or cyclic alkanediyl group and n is 1 or 2;

comprising the step of an alpha alkylation of an aldehyde of formula R—$CH_2$—CHO, wherein R has the same meaning as above, with an olefin compound being a fused or bridged bicyclic or tricyclic compound with a methylene group in alpha of a ring junction;

said step being performed in the presence of a photoredox catalyst, a hydrogen atom transfer donor, a secondary amine and light.

2. The process according to claim 1, characterized in that the aldehyde is propanal.

3. The process according to claim 1, characterized in that the olefin is a compound of formula

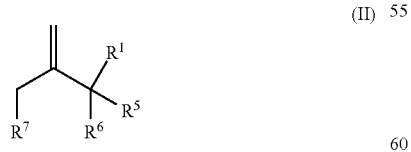

(II)

in a form of any one of its stereoisomers or a mixture thereof; and wherein $R^1$ represents a hydrogen atom or a $C_{1-2}$ linear alkyl group or a $C_{3-4}$ linear or branched alkyl group and $R^5$, $R^6$ and $R^7$ are taken together and represent a $C_{4-12}$ linear, branched or alicyclic alkanetryil.

4. The process according to claim 1, characterized in that the photoredox catalyst is an organic photocatalyst, or an iridium or a ruthenium complex.

5. The process according to claim 1, characterized in that the hydrogen atom transfer donor is a thiophenol of formula

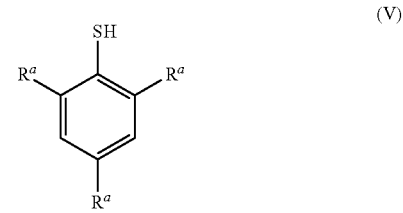

(V)

wherein each $R^a$ represents, independently from each other, a hydrogen atom, a halogen atom, a $C_{1-2}$ linear alkyl group, a $C_{3-4}$ linear or branched alkyl group, a phenyl group optionally substituted by one to five halogen atoms and/or $C_{1-4}$ alkyl or alkoxyl groups or a silyl group trisubstituted with $C_{1-4}$ alkyl groups or an aryl group; provided that at most two $R^a$ groups represent a hydrogen atom.

6. The process according to claim 1, characterized in that the compound of formula (I) is selected from the group consisting of 3-(4-isopropylcyclohex-1-en-1-yl)-2-methyl-propanal and 3-((S)-4-isopropylcyclohex-1-en-1-yl)-2-methylpropanal.

7. A composition of matter comprising:
a) a compound of formula

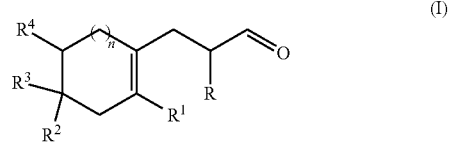

(I)

in a form of any one of its stereoisomers or a mixture thereof and wherein R represents a hydrogen atom or $C_{1-8}$ linear alkyl group; $R^1$, $R^2$, $R^3$ and $R^4$ represent, when taken separately, independently of each other, a hydrogen atom or a $C_{1-2}$ linear alkyl group or a $C_{3-4}$ linear or branched alkyl group or $R^2$ and $R^3$, when taken together, represent a $C_{4-10}$ linear, branched or cyclic alkanediyl group and n is 1 or 2; and
b) a compound of formula

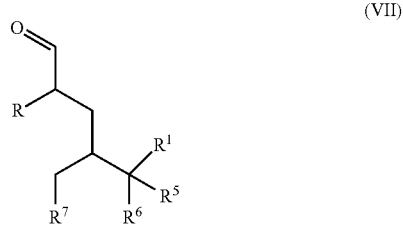

(VII)

in a form of any one of its stereoisomers or a mixture thereof; and wherein R represents a hydrogen atom or a $C_{1-8}$ linear alkyl group; $R^1$ represents a hydrogen atom or a $C_{1-2}$ linear alkyl group or a $C_{3-4}$ linear or branched alkyl group; and $R^5$, $R^6$ and $R^7$ are taken together and represent a $C_{4-12}$ linear, branched or alicyclic alkanetryil.

8. The composition of matter according to claim 7, characterized in that the compound of formula (VII) is a compound of

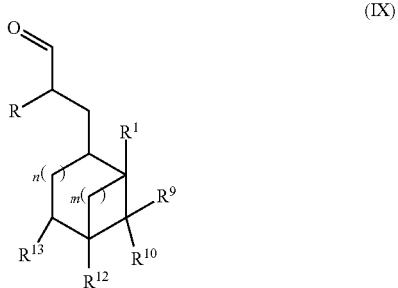

(IX)

in a form of any one of its stereoisomers or a mixture thereof; and wherein R represents a hydrogen atom or a $C_{1-8}$ linear alkyl group; n is 0 or 1; m is 1 or 2; $R^1$, $R^9$, $R^{10}$, $R^{12}$ and $R^{13}$ represent, when taken separately, independently from each other, a hydrogen atom or a $C_{1-2}$ linear alkyl group or a $C_{3-5}$ linear or branched alkyl.

9. The composition of matter according to claim 7, characterized in that the composition of matter comprises from 0.1 wt % to 50 wt % of compound of formula (VII), relative to a total weight of the composition.

10. A method to confer, enhance, improve or modify odor properties of a perfuming composition or of a perfumed article, which method comprises adding to said composition or article an effective amount of the composition of matter as defined in claim 7.

11. A method, which comprises using a perfuming ingredient of a composition of matter as defined in claim 7.

12. A perfuming composition comprising:
 i) at least a composition of matter as defined in claim 7;
 ii) at least one ingredient selected from the group consisting of a perfumery carrier and a perfumery base; and
 iii) optionally at least one perfumery adjuvant.

13. A perfumed consumer product comprising at least one composition of matter as defined in claim 7.

14. The perfumed consumer product according to claim 13, characterized in that the product is a perfume, a fabric care product, a body-care product, a cosmetic preparation, a skin-care product, an air care product or a home care product.

15. The perfumed consumer product according to claim 14, characterized in that the perfumed consumer product is a fine perfume, a splash or eau de perfume, a cologne, an shave or after-shave lotion, a liquid or solid detergent, a fabric softener, a fabric refresher, an ironing water, a paper, a bleach, a carpet cleaner, a curtaing care product, a shampoo, a coloring preparation, a color care product, a hair shaping product, a dental care product, a disinfectant, an intimate care product, a hair spray, a vanishing cream, a deodorant or antiperspirant, a hair remover, a tanning or sun product, a nail product, a skin cleansing, a makeup, a perfumed soap, shower or bath mousse, oil or gel, or a foot/hand care products, a hygiene product, an air freshener, a "ready to use" powdered air freshener, a mold remover, a furnisher care, a wipe, a dish detergent or hard-surface detergent, a leather care product or a car care product.

16. The process according to claim 4, characterized in that the photoredox catalyst is an iridium complex.

* * * * *